United States Patent [19]

Isogai et al.

[11] Patent Number: 4,925,794

[45] Date of Patent: May 15, 1990

[54] HYBRID PLASMIDS AND MICROORGANISMS CONTAINING THEM

[75] Inventors: Takao Isogai; Masaru Yoshida, both of Ibaraki, Japan

[73] Assignee: Fujisawa Pharmaceutical Co., Ltd., Osaka, Japan

[21] Appl. No.: 807,734

[22] Filed: Dec. 11, 1985

[30] Foreign Application Priority Data

Jan. 2, 1985 [GB] United Kingdom ............... 8500040
Oct. 17, 1985 [GB] United Kingdom ............... 8525667

[51] Int. Cl.$^5$ .................... C12P 19/34; C12N 15/00; C12N 1/16; C12N 1/00; C07H 15/12
[52] U.S. Cl. .............................. 435/91; 435/172.1; 435/172.3; 435/255; 435/320; 536/27; 935/19; 935/28; 935/56; 935/69
[58] Field of Search ................ 435/172.3, 253, 254, 435/49, 91, 172.1, 255, 320; 536/27

[56] References Cited

PUBLICATIONS

Zamir, A. et al., Proc. Nat'l Acad. Sci., U.S.A., vol. 78 (Jun. 1981) pp. 3496–3500.
Chan, C. S. M. and Tye, B. K., Proc. Nat'l Acad. Sci., U.S.A., vol. 77 (Nov. 1980) pp. 6329–6333.
Chemical Abstracts, vol. 101, 1984, p. 166, Abstract No. 105136f, Columbus, Ohio, U.S.; P. L. Skatrud et al., "Cloning of a DNA Fragment from Cephalosporium Acremonium which Functions as an Autonomous Replication Sequence in Yeast", & Curr. Genet, 1984 (Abstract).
Chemical Abstracts, vol. 102, 1985, p. 151, Abst. No. 180146h, Columbus, Ohio, U.S.; P. Tudzynski, "Procedure for the Development of Replicating Systems in Filamentous Fungi", & Dechema-Monogr., 1984, 95 (Biotechnol. 83: Mikrob. Stoffprod., Neuentwickl, biotechnol., Gentech), 305-13 (Abstract).
Chemical Abstracts, vol. 104, 1986, p. 167, Abstract No. 103349b, Columbus, Ohio, U.S.; M. A. Penalva et al., "Studies on Transformation of Cephalosporium Acremonium", & UCLA Symp. Mol. Cell. Biol. New Ser. 1985, 34 (Mol. Genet Filamentous Fungi), 59–68 (Abstract).
Current Genetics, vol. 5, Aug. 1982, pp. 227–321, Springer Verlag; W. Minuth et al., "Extrachromosal Genetics of Cephalosporium Acremonium, I. Characterization and Mapping of Mitochondrial DNA", (document).
Current Genetics (1982), 5:227-231.
Current Genetics (1982), 6:153-157.
Current Genetics (1984), 8:155-163.
Gene (1983), 243-252.

Primary Examiner—Thomas G. Wiseman
Assistant Examiner—Joan Ellis
Attorney, Agent, or Firm—Oblon, Spivak, McClelland, Maier & Neustadt

[57] ABSTRACT

New hybrid plasmids which are useful as vectors in recombinant DNA in which *Acremonium chrysogenum* or *Saccharomyces cerevisiae* is used as a host, and microorganisms bearing the hybrid plasmids, are disclosed. The disclosure herein is based on the cloning of autonomous replication sequences (ARS) of *A. chrysogenum* ATCC 11550 and introduction of the ARS into a shuttle vector of *E. coli* and *Saccharomyces cerevisiae* and construction of new types of plasmids based on the ARS.

7 Claims, 10 Drawing Sheets

```
            10         20         30         40         50         60         70
     GATCTCGGCG AGCGGGTGAC GGACGGGTTG CTAGCGTTTA CCAAGCCGGG TCACACGCCG CGGCTTGGCA
     CTAGAGCCGC TCGCCCACTG CCTGCCCAAC GATCGCAAAT GGTTCGGCCC AGTGTGCGGC GCCGAACCGT 80         90        100        110        120        130        140
     GGEAGCAGCC ACTGTTACTA CTTGCATGTG GGCTGATTGA AAATCCCGGA ACCGATGGAT GCTTCCCCCG
     CCETCGTCGG TGACAATGAT GAACGTACAC CCGACTAACT TTTAGGGCCT TGGCTACCTA CGAAGGGGGC 150        160        170        180        190        200        210
     GGGATGCCGC TTCTTTCTCT CTCTCGGCCG CGGGAAGGTA TGCGTTGCCC CCGGCCATAA TAGTCGTCAA
     CCCTACGGCG AAGAAAGAGA GAGAGCCGGC GCCCTTCCAT ACGCAACGGG GGCCGGTATT ATCAGCAGTT 220        230        240        250        260        270        280
     GCGGAAGGCC AGCATTTGAT CAGTAAAAAT ATCGGAATGA TAAGTAATAG ATTTTAAATT TACTATATTA
     CGCCTTCCGG TCGTAAACTA GTCATTTTTA TAGCCTTACT ATTCATTATC TAAAATTTAA ATGATATAAT 290        300        310        320        330        340        350
     TATTGTATTT TTTTCCCTAT TATTAGTTCT AATAAATAGG TCAATTTAGA TAATAATCTT ACTTTATTAA
     ATAACATAAA AAAAGGGATA ATAATCAAGA TTATTTATCC AGTTAAATCT ATTATTAGAA TGAAATAATT 360        370        380        390        400        410        420
     ATTTAAATTG ATTTAAAGAA TATAACAAAC TATATTTTCT CAAATAATTA AAATATTTCC CTGATTCATT
     TAAATTTAAC TAAATTTCTT ATATTGTTTG ATATAAAAGA GTTTATTAAT TTTATAAAGG GACTAAGTAA 430        440        450        460        470        480        490
     TTTAATTAAT TCATTCCACA TTTTTTTCAA AATAAGATGA TTTAATTTTA AAAATGTATT TAAGTATTTA
     AAATTAATTA AGTAAGGTGT AAAAAAAGTT TTATTCTACT AAATTAAAAT TTTACATAA  ATTCATAAAT 500        510        520        530        540        550        560
     AAAGTATAAT TAATGTATTT TCTTTTTTTT ATAAAATCTT TTACAAAAAA ATACTCATCA TACATTTTAT
     TTTCATATTA ATTACATAAA AGAAAAAAAA TATTTTAGAA AATGTTTTT  TATGAGTAGT ATGTAAAATA
```

```
        10         20         30         40         50         60         70
GATCTCGGCG AGCGGGTGAC GGACGGGTTG CTAGCGTTTA CCAAGCCGGG TCACACGCCG CGGCTTGGCA
CTAGAGCCGC TCGCCCACTG CCTGCCCAAC GATCGCAAAT GGTTCGGCCC AGTGTGCGGC GCCGAACCGT
        80         90        100        110        120        130        140
GGEAGCAGCC ACTGTTACTA CTTGCATGTG GGCTGATTGA AAATCCCGGA ACCGATGGAT GCTTCCCCCG
CCETCGTCGG TGACAATGAT GAACGTACAC CCGACTAACT TTTAGGGCCT TGGCTACCTA CGAAGGGGGC
       150        160        170        180        190        200        210
GGGATGCCGC TTCTTTCTCT CTCTCGGCCG CGGGAAGGTA TGCGTTGCCC CCGGCCATAA TAGTCGTCAA
CCCTACGGCG AAGAAAGAGA GAGAGCCGGC GCCCTTCCAT ACGCAACGGG GGCCGGTATT ATCAGCAGTT
       220        230        240        250        260        270        280
GCGGAAGGCC AGCATTTGAT CAGTAAAAAT ATCGGAATGA TAAGTAATAG ATTTTAAATT TACTATATTA
CGCCTTCCGG TCGTAAACTA GTCATTTTTA TAGCCTTACT ATTCATTATC TAAAATTTAA ATGATATAAT
       290        300        310        320        330        340        350
TATTGTATTT TTTTCCCTAT TATTAGTTCT AATAAATAGG TCAATTTAGA TAATAATCTT ACTTTATTAA
ATAACATAAA AAAAGGGATA ATAATCAAGA TTATTTATCC AGTTAAATCT ATTATTAGAA TGAAATAATT
       360        370        380        390        400        410        420
ATTTAAATTG ATTTAAAGAA TATAACAAAC TATATTTTCT CAAATAATTA AAATATTTCC CTGATTCATT
TAAATTTAAC TAAATTTCTT ATATTGTTTG ATATAAAAGA GTTATTAAT TTTATAAAGG GACTAAGTAA
       430        440        450        460        470        480        490
TTTAATTAAT TCATTCCACA TTTTTTTCAA AATAAGATGA TTTAATTTTA AAAATGTATT TAAGTATTTA
AAATTAATTA AGTAAGGTGT AAAAAAAGTT TTATTCTACT AAATTAAAAT TTTTACATAA ATTCATAAAT
       500        510        520        530        540        550        560
AAAGTATAAT TAATGTATTT TCTTTTTTTT ATAAAATCTT TTACAAAAAA ATACTCATCA TACATTTTAT
TTTCATATTA ATTACATAAA AGAAAAAAAA TATTTTAGAA AATGTTTTTT TATGAGTAGT ATGTAAAATA
```

*FIG. 8A*

```
      570        580        590        600        610        620        630
ATTTTTATA  TAAAAGAGAA  TAAATATTT  TTATATAATT  ATTGTACAAA  GAAGTATAAT  TCTTAAACAA
TAAAAAATAT ATTTTCTCTT  ATTTATAAAA AATATATTAA  TAACATGTTT  CTTCATATTA  AGAATTGTT
      640        650        660        670        680        690        700
GTTATAAGTT ATTCTCATAT  TTAATAGATG ATATTTCTT   TTTAATGCTT  TTTTTCTTT   ATTTATAGTA
CAATATTCAA TAAGAGTATA  AATTATCTAC TATAAAAGAA  AAATTACGAA  AAAAAAGAAA  TAAATATCAT
      710        720        730        740        750        760        770
AATAGTGTTA TTTTTGCTTT  ACTATTGTA  TATTTTATAT  TAGCATCACT  TACAAAAATT  CTTCTTAAAA
TTATCACAAT AAAAACGAAA  TGATAAACAT ATAAAATATA  ATCGTAGTGA  ATGTTTTAA   GAAGAATTT
      780        790        800        810        820        830        840
AATTACGTCT TTTTTTAGA   TATATAAATT TAGTTTTACC  TAAAAATTGA  CGGTTTTAA   AAAATAAATT
TTAATGCAGA AAAAAAATCT  ATATATTTAA ATCAAAATGG  ATTTTTAACT  GCCAAAAATT  TTTTATTTAA
      850        860        870        880        890        900        910
AAAATAACTT TTAATTATT   TATTTATATT TACAGTATTA  GCTGGTATAT  TTTTCATATT  ATTTTTATTA
TTTTATTGAA AATTAATAAA  ATAAATATAA ATGTCATAAT  CGACCATATA  AAAAGTATAA  TAAAAATAAT
      920        930        940        950        960        970        980
AAAGAATATA TAACATTTTT  TCATTCTTTT GAAAAGCAG   GTAAATATTT  CATATTATTT  ATAACAGTTA
TTTCTTATAT ATTGTAAAAA  AGTAAGAAAA CTTTTCGTC   CATTTATAAA  GTATAATAAA  TATTGTCAAT
      990       1000       1010       1020       1030       1040       1050
ATTTAGGTTT TAAACCAGAA  GTTCTGATAT TTTTATTAA   ATTATTCTTA  AAAATTTCA   TTTTTATTTA
TAAATCCAAA ATTGGTCTT   CAAGACTATA AAAATAAATT  TAATAAGAAT  TTTTAAAAGT  AAAAATAAAT
     1060       1070       1080       1090       1100       1110       1120
TTATTTATTT CTTTTTATTT  CTTTTATAT  GCTTATTATA  GCTTTAACCT  ATAGCCATAA  AAATGTTGGG
AATAAATAAA GAAAAATAAA  GAAAAATATA CGAATAATAT  CGAAATTGGA  TATCGGTATT  TTTACAACCC
```

*FIG. 8B*

```
         1130              1140              1150              1160              1170              1180              1190
TAGTTTAAAA GGATTATCAT GTATTGCATA ACATTCACCT TATAGTCGTT GAACGTTTTT ATTTTATAAC
ATCAAATTT  CCTAATAGTA CATAACGTAT TGTAAGTGGA ATATCAGCAA CTTGCAAAAA TAAAATATTG
         1200              1210              1220              1230              1240              1250              1260
ATATGCTAAA ATAAATTCCG CTTCAAATTT ACTATCTTAA GTAATTTTJG AAATTTACCC AATTTATATC
TATACGATTT TATTTAAGGC GAAGTTTAAA TGATAGAATT CATTAAAAKC TTTAAATGGG TTAAATATAG
         1270              1280              1290              1300              1310              1320              1330
AATTATTTTA AGAGCTCTTA GCTCAAATAA AATATTAAAG GACAAACATC CCTAGCGTAG CTTTTCCAAT
TTAATAAAAT TCTCGAGAAT CGAGTTTATT TTATAATTTC CTGTTTGTAG GGATCGCATC GAAAAGGTTA
         1340              1350              1360              1370              1380              1390              1400
AATCCAAGAT CCGTTAAATT ATCGATGCTA TTTATACCTT AACAAGTGCT CTGTTACGAG ATC
TTAGGTTCTA GGCAATTTAA TAGCTACGAT AAATATGGAA TTGTTCACGA GACAATGCTC TAG (E : C or deletion, F : G or deletion, J : T or deletion, K : A or deletion)
```

FIG. 8C

HYBRID PLASMIDS AND MICROORGANISMS CONTAINING THEM

BACKGROUND OF THE INVENTION

1. Field of the Invention

The present invention relates to new hybrid plasmids which are useful as vectors in recombinant DNA work in which *Acremonium chrysogenum* or *Saccharomyces cerevisiae* is used as a host, and to microorganisms bearing said hybrid plasmids.

2. Description of the Related Art

It is well known that *Escherichia coli* (*E. coli*) host-vector system is useful for recombinant DNA work.

However, the *E. coli* host-vector system is not satisfactory for production of substances which are produced by higher animals.

On the other hand, *Acremonium chrysogenum* ATCC 11550 (*A. chrysogenum* ATCC 11550) is used in the manufacture of many clinically important semi-synthetic cephalosporin antibiotics. Further, it is known that *A. chrysogenum* ATCC 11550 produces extracellularly an alkaline protease in large amounts (over 1 g/l) [J. Ferment. Technol. 50(9) 592–599 (1972)].

SUMMARY OF THE INVENTION

The inventors of the present invention, as a result of extensive study, have succeeded in cloning two autonomous replication sequences (ARS) of *A. chrysogenum* ATCC 11550 and in introducing the ARS into a shuttle vector of *E. coli* and *Saccharomyces cerevisiae* (*S. cerevisiae*), and then in constructing new types of plasmids which are useful as vectors in recombinant DNA work in which *A. chrysogenum* or *S. cerevisiae* is used as a host.

Accordingly, one object of the present invention is to provide new DNA fragments of *A. chrysogenum* ATCC 11550 which function as an autonomous replication sequence (ARS) in *S. cerevisiae* and *A. chrysogenum*.

Another object of the present invention is to provide new types of hybrid plasmids pLEU135, pLEU97, pCEP97 and pCYG97 which are useful as vectors in recombinant DNA work in which *A. chrysogenum* or *S. cerevisiae* is used as a host.

A further object of the present invention is to provide new microorganisms bearing said new plasmids.

BRIEF DESCRIPTION OF THE DRAWINGS

To facilitate understanding the present invention, the plasmids obtained according to the present invention are represented in the attached figures in which

FIG. 8 represents the DNA sequence of the ARS of the plasmid pCYG97.

DESCRIPTION OF THE PREFERRED EMBODIMENTS

Plasmids pLEU135, pLEU97, pCEP97 and pCYG97 according to the present invention which are characterized by the restriction enzyme cleavage maps shown in FIGS. 3, 4, 5 and 6, respectively, are prepared by known techniques.

The following are general methods for preparations of pLEU135, pLEU97, pCEP97 and pCYG97.

(1) The nutrition marker, the gene LEU+ of plasmid YEp13 is introduced into the PstI site of plasmid pBR325 to give plasmid pBR-LEU, which is used as a vector for detecting autonomous replication sequences (ARS).

The well-known plasmid pBR 325 is used as a starting material.

The plasmid YEp13 is a known shuttle vector of *E. coli* and *S. cerevisiae* [J. R. Broach et al. Gene 8 (1979) 121].

The plasmids pBR325 and YEp13 are separately digested with restriction enzyme PstI and the resulting reaction mixtures are combined and then ligated with T4 DNA ligase.

The resulting ligated DNA was inserted into *E. coli* C600r$^-$m$^-$ (ATCC 33525) and then Ap$^S$Tc$^R$Cm$^R$Leu+ colonies are selected.

Figure 7:
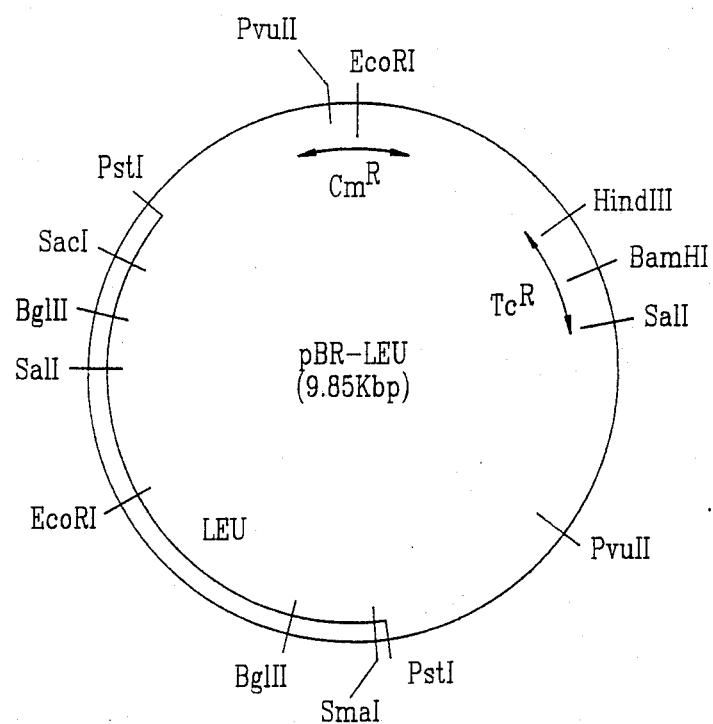
FIG. 7 represents a restriction enzyme cleavage map for pBR-LEU.

The plasmid thus constructed is named pBR-LEU which is characterized by the restriction enzyme map shown in FIG. 7.

(2) The chromosomal DNA of *A. chrysogenum* ATCC 11550 which is obtained by treating cells of the said microorganism with an enzyme capable of lysing a cell wall such as Zymolyase (Seikagaku Kogyo Co), and then treating the resulting protoplast with phenol and chloroform, is partially digested with the restriction enzyme Sau 3A and purified with sucrose density gradient ultra-centrifugation to give about 1–10 Kbp DNA fragments.

(3) The 1–10 Kbp DNA fragments are introduced into the BamHI site of the plasmid pBR-LEU (obtained in the above (1)) as follows:

The plasmid pBR-LEU is digested with restriction enzyme Bam HI and said 1–10 Kbp DNA fragments are added to the resulting digested mixture and then ligated with T4 DNA ligase.

The ligated DNA is inserted into *E. coli* C600r$^-$m$^-$ (ATCC 33525) and then Tc$^S$Cm$^R$Leu+ colonies are selected by conventional methods.

The resulting Cm$^R$Tc$^S$Leu+ hybrid plasmid DNAs are inserted into *S. cerevisiae* SHY 3 (ATCC 44771) [Proc. Natl. Acad. Sci. U.S.A. 75 (1978) 1929].

The hybrid plasmids which give high-frequency Leu+ transformants, are selected to give two hybrid plasmid DNAs containing ARS of *A. chrysogenum* ATCC 11550.

The resulting two hybrid plasmids are named pLEU135 and pLEU97, respectively.

(4) The plasmid pLEU97, obtained in the above (3), is digested with a restriction enzyme PstI and the resulting digestion is ligated with T4 DNA ligase to give plasmid pCEP97 lacking the gene Leu+.

(5) PvuII Km$^R$ fragment of Tn903 is introduced into the plasmid pCEP97, obtained in the above (4), to give the plasmid pCYG97 as follows:

The PvuII fragment of Tn903 is a known Km$^R$ gene [A. Oka et al. J. Mol. Biol. 147 (1981) 217].

The pCEP97 DNA is partially digested with restriction enzyme PvuII and the resulting digested pCEP97 DNA and the PvuII Km$^R$ fragment are ligated with T4 DNA ligase.

The resulting ligated DNA is inserted into *E. coli* C600r$^-$m$^-$ (ATCC 33525) and Ap$^R$Km$^R$Cm$^R$clone is obtained according to a conventional manner and the resulting plasmid is named pCYG97.

Figure 6:
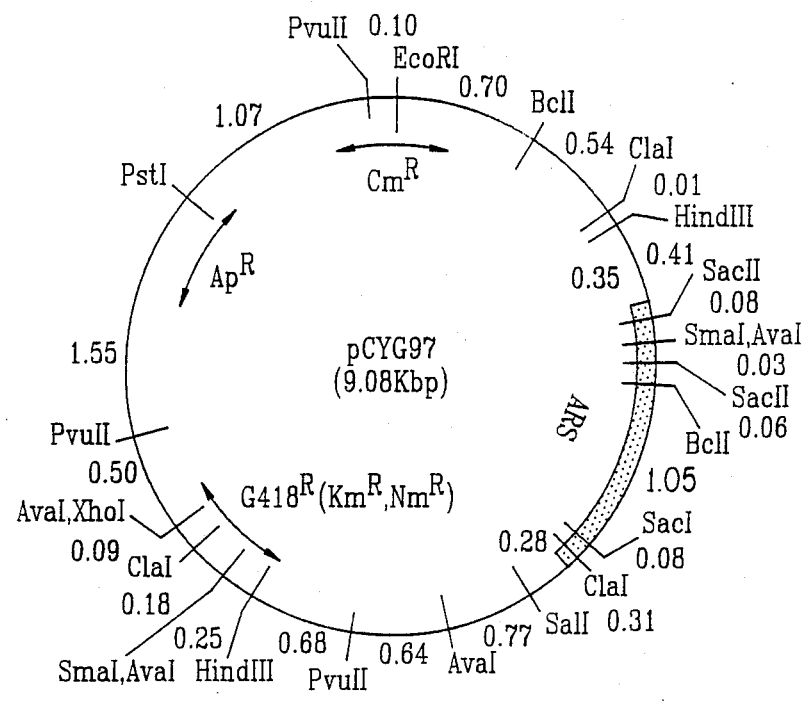
FIG. 6 represents a restriction enzyme cleavage map for pCYG97.

The plasmid pCYG97, as shown in FIG. 6, contains ARS DNA of *A. chrysogenum* ATCC 11550 and the Kanamycin-resistant gene (Km$^R$) of Tn903 of *E. coli*.

The plasmid pCYG97 can transform *S. cerevisiae* YNN 27 [D. T. Stinchcomb et al. Proc. Natl. Acad. Sci. U.S.A. 77 (1980) 4559] and the resulting transformations are directly selected in the agar plate containing the aminoglycoside antibiotic G418.

Figure 3:
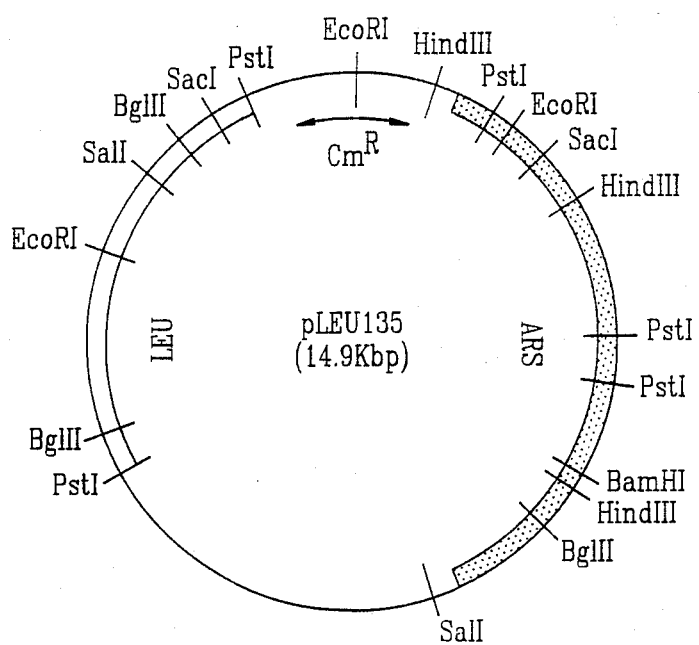
FIG. 3 represents a restriction enzyme cleavage map for pLEU135.

The plasmid pLEU135 constructed as above is characterized by the restriction enzyme cleavage map as shown in FIG. 3.

The molecular size of the pLEU135, which is measured by agarose gel electrophoresis method, is about 14.9 Kbp.

The autonomous replication sequence (ARS) in the plasmid pLEU135 shows a unique restriction enzyme cleavage pattern and the molecular size, which is measured by agarose gel electrophoresis, is about 5.04 Kbp and is a new DNA. Accordingly, the plasmid pLEU135 containing said new ARS DNA is a new plasmid.

Figure 4:
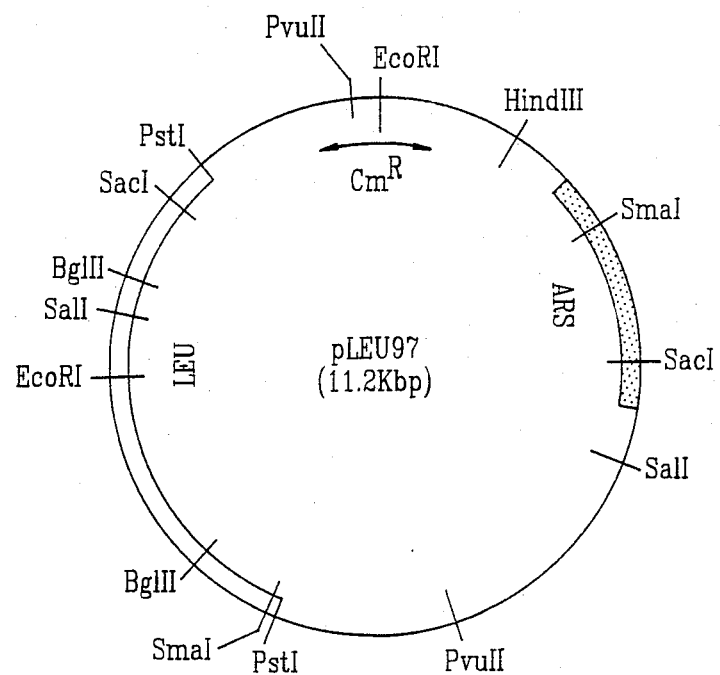
FIG. 4 represents a restriction enzyme cleavage map for pLEU97.

The plasmid pLEU97, constructed as above, is characterized by the restriction enzyme cleavage map as shown in FIG. 4.

The molecular size of the pLEU97, which is measured by agarose gel electrophoresis, is about 11.2 Kbp.

The autonomous replication sequence (ARS) in the plasmid pLEU97 (the same in plasmids pCEP97 and pCYG97) shows a unique restriction enzyme cleavage pattern. The molecular size, when measured by agarose gel and polyacrylamide gel electrophoresis methods, is about 1.39 Kbp and is a new DNA.

Accordingly, the plasmid pLEU97 containing said new ARS DNA is a new plasmid.

Figure 5:
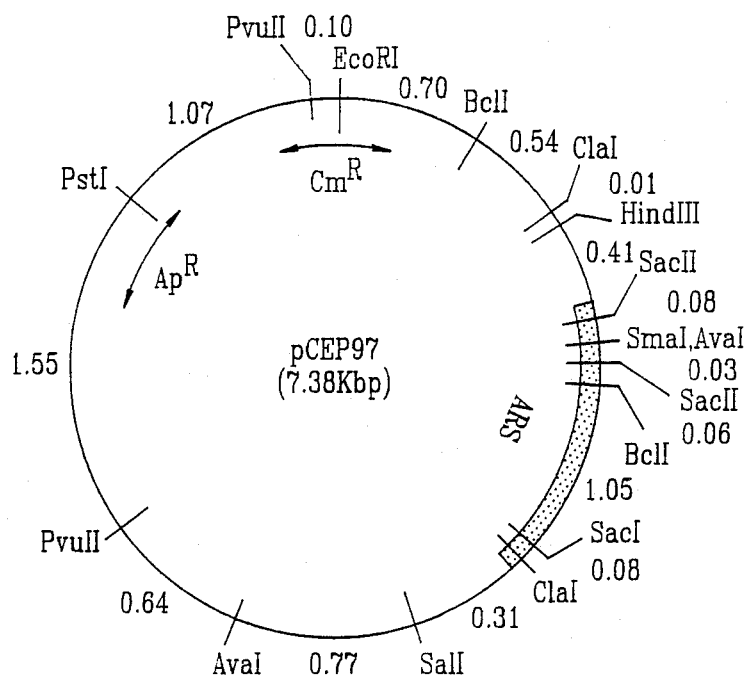
FIG. 5 represents a restriction enzyme cleavage map for pCEP97.

The plasmid pCEP97 which is obtained by digesting pLEU97 with restriction enzyme, PstI and by ligating the resulting digestion with T4 DNA ligase, is characterized by the restriction enzyme cleavage map as shown in FIG. 5.

The molecular size of pCEP97, which is measured by agarose gel and polyacrylamide gel electrophoresis methods, is about 7.38 Kbp.

The autonomous replication sequence (ARS) in the pCEP97 is the same as that in pLEU97.

Accordingly, the plasmid pCEP97 containing said new ARS is a new plasmid.

The plasmid pCYG97, constructed as above, is characterized by the restriction enzyme cleavage map as shown in FIG. 6.

The molecular size of the pCYG97, when measured by agarose gel and polyacrylamide gel electrophoresis methods, is about 9.08 Kbp.

The autonomous replication sequence (ARS) in the pCYG97 is the same as that in pLEU97.

Accordingly, the plasmid pCYG97 containing said ARS DNA and the kanamycin-resistant gene (Km$^R$) of Tn903 of *E. coli*, is a new plasmid.

The hybrid plasmids pLEU135, pLEU97, pCEP97 and pCYG97 according to the present invention have the following utility.

The plasmid pLEU135 containing the specific ARS DNA of *A. chrysogenum* ATCC 11550 is useful as a vector in recombinant DNA work in which *A. chrysogenum* or *S. cerevisiae* is used as a host and leucine is used as a selection marker.

The plasmid pLEU97 containing the specific ARS DNA of *A. chrysogenum* ATCC 11550 is useful as a vector in recombinant DNA work in which *A. chrysogenum* or *S. cerevisiae* is used as a host and leucine is used as a selection marker.

The plasmid pCEP97 per se containing the specific ARS DNA of *A. chrysogenum* ATCC 11550 is useful as an intermediate for constructing the plasmid pCYG97 and is also useful as a vector in recombinant DNA work in which *A. chrysogenum* or *S. cerevisiae* is used as a host, (by further introducing a proper selection marker into this pCEP97.)

The plasmid pCYG97 containing the specific ARS DNA of *A. chrysogenum* ATCC 11550 is useful as a vector in recombinant DNA work in which *A. chrysogenum* or *S. cerevisiae* is used as a host and the aminoglycoside antibiotic G418 resistance is used as a selection marker, and further in addition to the antibiotic G418 kanamycin and neomycin are also used as a selection markers in *A. chrysogenum*.

Accordingly, the plasmids pLEU135, pLEU97 and pCYG97 of the present invention are useful for modifying the properties of strains of microorganisms (e.g. improvement of productivity of cephalosporin c), particularly yeasts such as *S. cerevisiae* and fungi such as *A. chrysogenum* ATCC 11550.

Further, as described previously, *A. chrysogenum* ATCC 11550 produces extracellularly an alkaline protease in large amount (over 1 g/l). Accordingly, the plasmids pLEU135, pLEU97 and pCYG97 are useful for intermediates for construction of expression vectors which are used for extracellular production of human active peptides such as Human Tissue Plasminogen Activator (HTPA) in *S. cerevisiae* or *A. chrysogenum*, by cloning the gene of said alkaline protease.

The plasmids pLEU135, pLEU97, pCEP97 and pCYG97 constructed according to the present invention are each inserted into *E. coli* C600r$^-$m$^-$ (ATCC33525) and the following microorganisms are obtained.

*Escherichia coli* C600r$^-$m$^-$ (pLEU135)
*Escherichia coli* C600r$^-$m$^-$ (pLEU97)
*Escherichia coli* C600r$^-$m$^-$ (pCEP97)
*Escherichia coli* C600r$^-$m$^-$ (pCYG97)

The following examples are illustrative of the present invention.

In the descriptions of the examples, the following abbreviations are used.

ATP: adenosine-5'-triphosphate
DTT: dithiothreitol
Tris: tris(hydroxymethyl)aminomethane
EDTA: ethylenediaminetetraacetic acid
SDS: sodium laurylsulfate
PEG: polyethylene glycol
bp: base pair
Kbp: kilo-base pairs
ARS: Autonomous Replication Sequence
Ap$^R$: ampicillin resistant in *E. coli*
Ap$^S$: ampicillin sensitive in *E. coli*
Cm$^R$: chloramphenicol resistant in *E. coli*
Cm$^S$: chloramphenicol sensitive in *E. coli*
Tc$^R$: tetracycline resistant in *E. coli*
Tc$^S$: tetracycline sensitive in *E. coli*

Km$^R$: kanamycin resistant in *E. coli*
Nm$^R$: neomycin resistant in *E. coli*
Km$^S$: kanamycin sensitive in *E. coli*
G418$^R$: G418 resistant in *S. cerevisiae*
Leu$^+$: complementation of leucine auxotrophic mutants of *E. coli* leu B and *S. cerevisiae* leu 2
Buffer and Medium:
L;
  20 mM Tris-HCl (pH 7.5)
  10 mM MgCl$_2$
  6 mM 2-mercaptoethanol
  100 µg/ml Bovine Serum Albumin (BRL)
M; L buffer containing 50 mM NaCl
H; L buffer containing 100 mM NaCl
S; L buffer containing 20 mM KCl
TE buffer;
  20 mM Tris-HCl (pH 7.5)
  0.5 mM EDTA
TPE buffer;
  36 mM Tris
  30 mM NaH$_2$PO$_4$
  1 mM EDTA
  pH 7.8
KP buffer;
  74.56 g/l KCl
  0.25 g/l K$_2$SO$_4$
  0.20 g/l MgCl$_2$.6H$_2$O
  0.05 g/l KH$_2$PO$_4$
  0.37 g/l CaCl$_2$.2H$_2$O
  25 mM Tris-HCl (pH 7.2)
YP buffer;
  1M KCl
  10 mM Tris-HCl (pH 7.5)
2M sorbitol buffer;
  2M sorbitol
  10 mM Tris-HCl (pH 7.5)
  10 mM CaCl$_2$
LB agar;
  10 g/l Bactotryptone (DIFCO)
  5 g/l Yeast Extract (DIFCO)
  5 g/l NaCl
  15 g/l Agar (DIFCO)
  pH 7.2
MM agar;
  10.5 g/l K$_2$HPO$_4$
  4.5 g/l KH$_2$PO$_4$
  1.0 g/l (NH$_4$)$_2$SO$_4$
  0.5 g/l Na$_3$.Citrate.2H$_2$O
  1.2 g/l MgSO$_4$.7H$_2$O
  2 g/l Glucose
  15 g/l Agar (DIFCO)
AC medium;
  36 g/l Sucrose
  27 g/l Glucose
  3 g/l L-Methionine
  7.5 g/l (NH$_4$)$_2$SO$_4$
  13.8 g/l KH$_2$PO$_4$
  14.0 g/l K$_2$HPO$_4$
  10 g/l Peptone (DIFCO)
YEPD medium;
  10 g/l Yeast Extract (DIFCO)
  20 g/l Peptone (DIFCO)
  20 g/l Glucose
Supplemented MM medium (lacking leucine) for yeast:
  10 g/l Glucose
  6.7 g/l Yeast Nitrogen Base (DIFCO)
  218 g/l Sorbitol
  10 mg/l Adenine
  10 mg/l Uracil
  40 mg/l Histidine
  40 mg/l Tryptophan
Regeneration Agar;
  YEPD medium containing 1.2M sorbitol and 3% agar
YEPD Base Plate;
  YEPD medium containing 1.2M sorbitol, 2% agar, 0.2% (W/V) potassium phosphate monobasic
YEPD Agar;
  YEPD medium containing 1.2M sorbitol and 2% agar For cleavage of various plasmids with restriction enzymes, the following combinations of restriction enzymes and buffers are employed as follows.

| Restriction enzyme | Buffer |
| --- | --- |
| AvaI, ClaI, EcoRI, HincII, HindIII, MluI, PstI, PvuII, SalI, XhoI | H buffer |
| AatII, SphI | M buffer |
| AccI, BamHI, BglII, HpaI, KpnI, SacI, SacII | L buffer |
| SmaI | S buffer |

Example 1

Construction of pLEU97 and pLEU135

(1) Construction of vector pBR-LEU

One µg of vector pBR325 DNA which was obtained as commercial preparation from Bethesda Research Laboratories/(BRL) was digested with 3 units of PstI in 10 µl of H buffer for an hour.

On the other hand, 1 µg of vector YEp13 DNA which was prepared according to the method described in J. R. Broach et al. Gene 8 (1979) 121, (was digested with 3 units of PstI in 10 µl of H buffer for an hour.) The above two reaction mixtures were combined and incubated in 0.5 units of T4 DNA ligase, 0.5 mM ATP and 10 mM DTT at 4° C. for 20 hours.

The ligated DNA thus obtained was used to transform *Escherichia coli* C600r$^-$m$^-$ (ATCC 33525) according to the method described in Molecular Cloning, page 250 (Cold Spring Harbor Laboratory, 1982).

The resulting transformed cells were plated on LB agar containing 5 µg/ml of tetracycline and incubated at 37° C. overnight. The tetracycline resistant colonies were transferred to LB agar containing 20 µg/ml of chloramphenicol, to LB agar containing 50 µg/ml of ampicillin and to MM agar containing 50 µg/ml threonine (lacking leucine), respectively and cultured at 37° C. overnight. The Ap$^S$Tc$^R$Cm$^R$Leu$^+$ colonies were obtained and the plasmid DNA was named pBR-LEU.

The pBR-LEU DNA was isolated according to the method described in Advanced Bacterial Genetics, page 116 (Cold Spring Harbor Laboratory, 1980).

(2) Cloning of ARS from *Acremonium chrysogenum* ATCC 11550 DNA (1) Extraction of ATCC 11550 DNA Sterile AC medium (100 ml) was inoculated with mycelium from an agar slant of *A. chrysogenum* ATCC 11550 and cultured for 3 days at 25° C., 250 rpm in 500 ml shaking flask. Cells were harvested and washed with KP buffer. The cells were suspended in 20 ml of KP buffer containing 10 mM DTT and incubated for 30 minutes at 37° C. Then 20 mg of Zymolyase 60,000 (Seikagaku Kogyo Co.) was added to the suspension and which was shaken for 2 hours at 37° C. The cells were centrifuged at 1,000×g for 10 minutes. The precipitate was suspended in 10 ml of 50 mM Tris-HCl buffer (pH 7.5) containing 10 mM EDTA and 1% SDS, and then extracted twice with equal volume of phenol and chloroform. The DNA solution was treated with 10 μg/ml of RNase A(Sigma) and then with 200 μg/ml of Protease K(Meck). The DNA solution was extracted with equal volume of phenol and precipitated with two volumes of ethanol at −20° C. for 2 hours. The precipitate was collected by centrifugation and resuspended in 0.5 ml of TE buffer. The DNA solution was extensively dialysed against the same buffer to give about 50 μg DNA.

Figure 1:
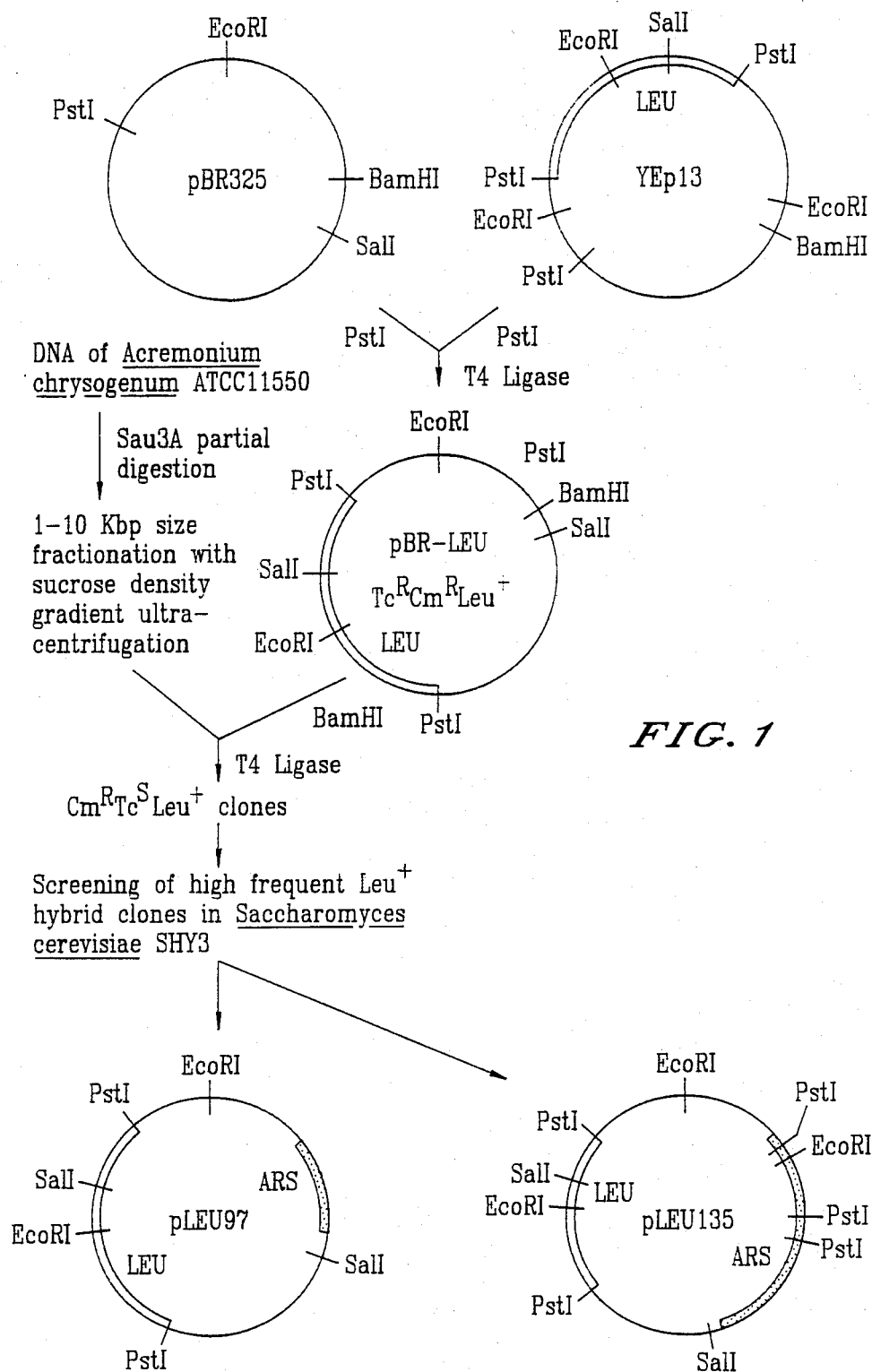
FIG. 1 represents the construction scheme of pLEU135 and pLEU97.

(2) Cloning of ATCC 11550 DNA to pBR-LEU BamHI site (FIG. 1).

About 10 μg of ATCC 11550 DNA, prepared as described in the above (1), was digested with one unit of Sau3A(BRL) in 200 μl of L buffer for 10 minutes. The reaction was terminated by heating at 65° C. for 10 minutes. The digested DNA was purified to about 1–10 Kbp in size with sucrose density gradient ultra-centrifugation. The size-fractionated DNA was suspended in 10 μl of TE buffer.

One μg of pBR-LEU DNA, prepared as described in the above (1), was digested with one unit of BamHI (BRL) in 10 μl of L buffer for an hour. The resulting digested sample and the size-fractionated DNA suspension in TE buffer prepared above were mixed. T4 DNA ligase (BRL) (0.5 unit), one μl of 10×L buffer, and 2 μl of 5 mM ATP and 100 mM DTT were added to the mixture. Subsequently, the resulting mixture was incubated at 4° C. for 20 hours. The ligated DNA was used to transform $E.\ coli$ C600r−m− (ATCC 33525) according to the method described in Molecular Cloning, page 250. The transformed cells were plated on LB agar containing 20 μg/ml of chloramphenicol and incubated at 37° C. overnight. The resulting chloramphenicol resistant colonies were transferred to LB agar containing 5 μg/ml of tetracycline and to MM agar containing 50 μg/ml of threonine (lacking leucine), respectively. $Tc^SCm^RLeu^+$ colonies were obtained (108 clones) and the plasmid DNAs were isolated according to the method described in Advanced Bacterial Genetics, page 116.

(3) Transformation to *Saccharomyces cerevisiae* SHY3 (ATCC 44771) (FIG. 1)

*S. cerevisiae* SHY3 (ATCC 44771) was transformed according to the method of Hinnen et al. (Proc. Natl. Acad. Sci. USA 75 (1978) 1929). A sterile YEPD medium (50 ml) containing 10 μg/ml of adenine and uracil was inoculated from an agar slant of *S. cerevisiae* SHY3 (ATCC 44771) and cultured at 30° C. overnight in 250 ml shaking flask. Cells were harvested by centrifugation, suspended in 5 ml of 1.2M sorbitol solution containing 25 mM EDTA and 50 mM DTT, and gently shaken at 30° C. for 10 minutes. Then the cells were harvested by centrifugation, washed with 1.2M sorbitol solution, suspended in 5 ml of 67 mM phosphate buffer (pH 7.5) containing 1.2M sorbitol, 10 mM EDTA and 200 μg/ml Zymolyase 60,000 (Seikagaku Kogyo Co.), and gently shaken at 30° C. for 60 minutes. The protoplasts were harvested by low speed centrifugation, washed with 1.2M sorbitol solution and suspended in 4 ml of 1.2M sorbitol solution containing 10 mM CaCl$_2$.

The protoplast suspension (0.2 ml) and $Cm^RTc^SLeu^+$ hybrid plasmid DNA, prepared in the above 2), (20 μl) (about 5 μg) were mixed and incubated at room temperature for 20 minutes. Two ml of 20% PEG 4,000 solution containing 10 mM CaCl$_2$ and 10 mM Tris-HCl (pH 7.5) was added to the suspension and the suspension was incubated at room temperature for 20 minutes. The transformed protoplasts were harvested by low speed centrifugation and suspended in 0.5 ml of 10 mM Tris-HCl buffer (ph 7.5) containing 1.2M sorbitol and 10 mM CaCl$_2$. The transformed cells (0.1 ml) were diluted into 10 ml of supplemented MM medium containing 3% agar (lacking leucine) for yeast, poured on top of a base plate (20 ml) of the same medium containing 2% agar and incubated at 30° C. for 4 days. About 500 colonies were obtained from two hybrid plasmid DNAs, but only one colony was obtained from other 106 hybrid plasmid DNAs and pBR-LEU DNA. The two hybrid plasmid DNAs containing ARS of *A. chrysogenum* ATCC 11550 were obtained from these results and named pLEU97 and pLEU135, respectively.

The effects of pLEU97 and pLEU135 DNA amounts on the frequency of transformation in *S. cerevisiae* SHY3 (ATCC 44771) are illustrated in Table 1-1 compared with pBR-LEU and YEp13 DNAs. YEp13 DNA contains the 2 μm plasmid DNA for replication in *S. cerevisiae*.

TABLE 1-1

Dose Response of pLEU97 and pLEU135 DNA Transformation in *S. cerevisiae* SHY3 (ATCC 44771)

| DNA | DNA Amount (mcg) | LEU$^+$ Transformants (CFU[1]) |
|---|---|---|
| pLEU97 | 7.5 | 5.4 × 10$^3$ |
|  | 3.0 | 1.6 × 10$^3$ |
|  | 1.5 | 5.3 × 10$^2$ |
| pLEU135 | 6.0 | 1.1 × 10$^3$ |
|  | 2.4 | 4.7 × 10$^2$ |
|  | 1.2 | 2.1 × 10$^2$ |
| pBR-LEU | 6.0 | 1 |
|  | 2.4 | 1 |
|  | 1.2 | 1 |
| YEp13 | 7.5 | 2.5 × 10$^3$ |
|  | 3.0 | 1.1 × 10$^3$ |
|  | 1.5 | 5.0 × 10$^2$ |

[1]CFU; colony forming units.

(3) Agarose gel electrophoretic analysis of pBR-LEU, pLEU135 and pLEU97 DNAs.

(1) Determination of a restriction enzyme map for pBR-LEU DNA

Determination of a restriction enzyme map for pBR-LEU DNA, prepared as described above, was carried out by cleavage with various restriction enzymes as specified in Table 1-2. Said restriction enzymes were obtained as commercial preparations from Bethesda Research Laboratories, Takara Shuzo Co. and Toyobo Co. pBR-LEU DNA (0.5–1 μg) and each of restriction enzymes (3–6 units) as specified in Table 1-2 were incubated in 20 μl of H buffer or L buffer at 37° C. for 60–180 minutes.

The digested samples were applied to 0.8% agarose gels and were electrophoresed for 2 to 3 hours at 80 V in TPE buffer in a vertical gel electrophoresis system (0.3×16×16 cm).

Detection of DNA bands in agarose gel was performed as described in Molecular Cloning, page 161 (1982). The molecular sizes of restriction DNA fragments were determined by comparing their relative mobilities in agarose gels with those of λ-HindIII fragments [L. H. Robinson and A. Landy Gene 2 (1977) 1].

Results of agarose gel electrophoretic analysis of pBR-LEU DNA cleaved with restriction enzymes are summarized in Table 2. Molecular sizes of pBR-LEU DNA restriction fragments are shown in Table 1-2. The cleavage map for restriction enzymes for pBR-LEU DNA is shown in FIG. 7.

TABLE 1-2

| Restriction Enzyme | Molecular Sizes[1] of pBR-LEU DNA Restriction Fragments[2]. | | |
|---|---|---|---|
| | A | B | Total |
| PstI | 6.00 | 3.85 | 9.85 |
| SalI | 5.72 | 4.13 | 9.85 |
| EcoRI | 6.85 | 3.00 | 9.85 |
| BglII | 7.20 | 2.65 | 9.85 |
| PvuII | 6.46 | 3.39 | 9.85 |
| KpnI | 7.45 | 2.40 | 9.85 |
| HpaI | 7.75 | 2.10 | 9.85 |

[1]Fragment sizes are expressed in Kbp.
[2]Fragment of smaller size was not determined.

(2) Determination of the restriction enzyme map for pLEU135 and pLEU97 DNAs.

Cleavage of the pLEU135 and pLEU97 DNAs with various restriction enzymes, as specified in Table 2, and agarose gel electrophoresis were performed according to the same method as the pBR-LEU DNA above. The results of the agarose gel electrophoretic analysis of the pLEU135 and pLEU97 DNAs cleaved with 11 restriction enzymes are summarized in Table 2. The number of restriction enzyme target sites of ARS DNA fragment was determined by comparison with those of pLEU97 and pBR-LEU DNAs, and with those of pLEU135 and pBR-LEU DNAs.

The molecular sizes of pLEU135 and pLEU97 DNA restriction fragments are shown in Tables 3 and 4, respectively. The cleavage map for the restriction enzymes of the pLEU135 and pLEU97 DNA are shown in FIGS. 3 and 4, respectively.

TABLE 2

| Restriction Enzyme Target Sites of pLEU97 and pLEU135 DNA | | | | |
|---|---|---|---|---|
| Restriction Enzyme | Sequence | Number of Restriction Enzyme Target Sites[1] | | |
| | | pLEU97 | pLEU135 | pBR-LEU |
| BamHI | G↓GATCC | 0 (0)[2] | 1 (1)[2] | 1 |
| BglII | A↓GATCT | 2 (0) | 3 (1) | 2 |
| EcoRI | G↓AATTC | 2 (0) | 3 (1) | 2 |
| HindIII | A↓AGCTT | 1 (0) | 3 (2) | 1 |
| HpaI | GTT↓AAC | 2 (0) | 3 (1) | 2 |
| KpnI | GGTAC↓C | 2 (0) | 2 (0) | 2 |
| PstI | CTCGA↓G | 2 (0) | 5 (3) | 2 |
| PvuII | CAG↓CTG | 2 (0) | 4 (2) | 2 |
| SacI | GAGCT↓C | 2 (1) | 2 (1) | 1 |
| SalI | G↓TCGAC | 2 (0) | 2 (0) | 2 |
| SmaI | CCC↓GGG | 2 (1) | 1 (0) | 1 |

(1) Restriction enzyme target sites were determined with 0.8% agarose gel electrophoresis. Fragments of smaller size was not examined.
(2) ( ); Number of restriction enzyme target sites of ARS DNA fragment.

TABLE 3

| Restriction Enzyme | Molecular Sizes[1] of pLEU135 DNA Restriction Fragments[2]. | | | | | |
|---|---|---|---|---|---|---|
| | A | B | C | D | E | Total |
| BglII | 7.63 | 4.62 | 2.65 | | | 14.9 |
| EcoRI | 9.83 | 2.99 | 2.08 | | | 14.9 |
| HindIII | 10.8 | 2.55 | 1.56 | | | 14.9 |
| KpnI | 12.5 | 2.40 | | | | 14.9 |
| PstI | 5.71 | 3.85 | 3.10 | 1.75 | 0.49 | 14.9 |
| SacI | 10.9 | 3.96 | | | | 14.9 |
| SalI | 9.19 | 5.71 | | | | 14.9 |

[1]Fragment sizes are expressed in Kbp.
[2]Fragments of smaller size was not determined.

TABLE 4

| Restriction Enzyme | Molecular Sizes[1] of pLEU97 DNA Restriction Fragments[2]. | | |
|---|---|---|---|
| | A | B | Total |
| BglII | 8.58 | 2.65 | 11.2 |
| EcoRI | 8.23 | 3.00 | 11.2 |
| HpaI | 9.13 | 2.10 | 11.2 |
| KpnI | 8.83 | 2.40 | 11.2 |
| PstI | 7.38 | 3.85 | 11.2 |
| PvuII | 6.46 | 4.77 | 11.2 |
| SacI | 6.82 | 4.42 | 11.2 |
| SalI | 5.72 | 5.51 | 11.2 |
| SmaI | 6.75 | 4.49 | 11.2 |

[1]Fragment sizes are expressed in Kbp.
[2]Fragments of smaller size was not determined.

Example 2

Construction of pCYG97 and pCEP97

(I) Construction of pCEP97.

Figure 2:
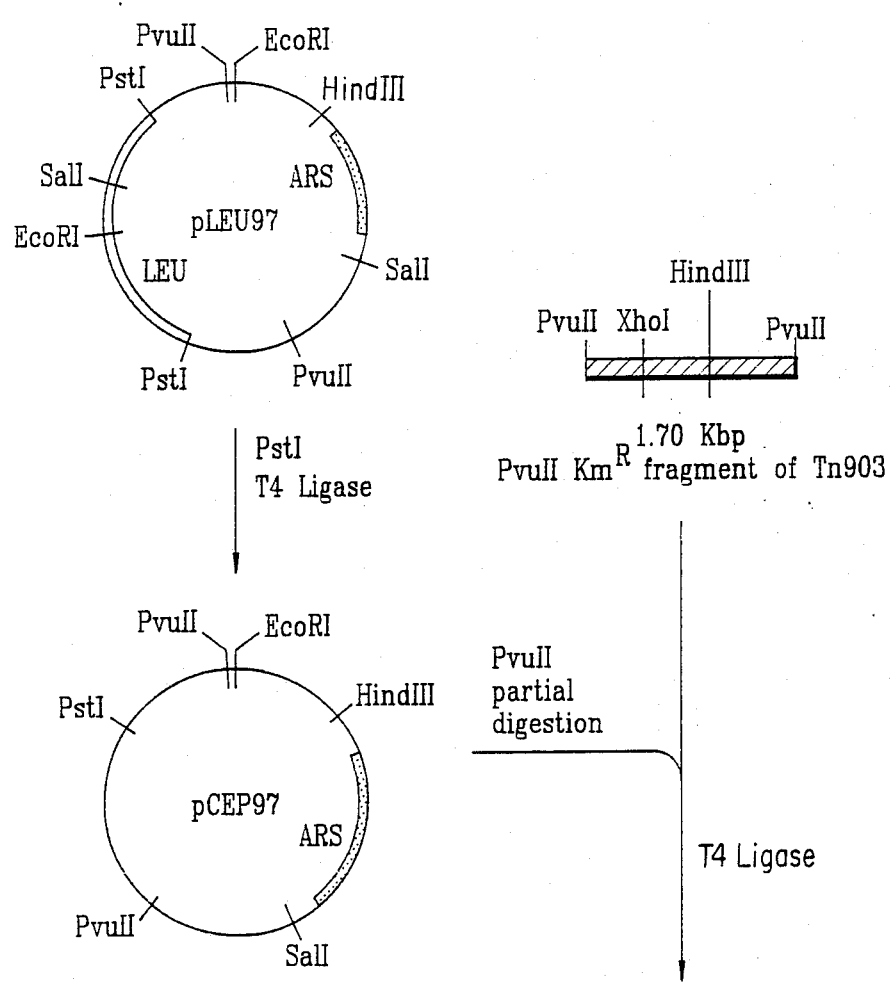
FIG. 2 represents the construction scheme of pCEP97 and pCYG97.
Figure 2:
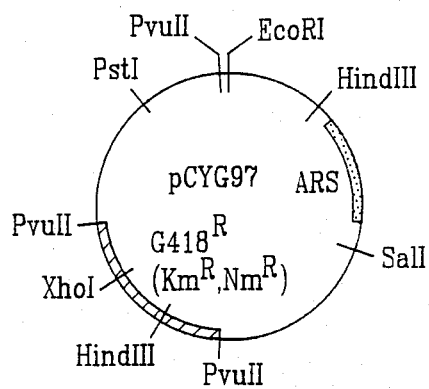

(1) Construction of pCEP97 from pLEU97 (FIG. 2).

pLEU97 DNA (3 μg), prepared as described in Example 1, was digested with 10 units of PstI in 20 μl of H buffer for 3 hours. Subsequently, 0.5 unit of T4 DNA ligase (BRL), and 2 μl of 5 mM ATP and 100 mM DTT were added to the reaction mixture. The resulting mixture was incubated at 4° C. for 20 hours. The ligated DNA was used to transform E. coli C600r⁻m⁻ (ATCC 33525) according to the method described in Molecular Cloning, page 250. The transformed cells were plated on LB agar containing 20 μg/ml of ampicillin and incubated at 37° C. overnight. About 500 ampicillin resistant colonies were obtained and named pCEP97. pCEP97 DNA was isolated according to the method described in Advanced Bacterial Genetics, page 116.

(2) Determination of a restriction enzyme map for pCEP97 DNA.

Determination of a restriction enzyme map for pCEP97 DNA, prepared as described in the above (1), was carried out by cleavage with various restriction enzymes as specified in Table 5. Said restriction enzymes were obtained as commercial preparation from Bethesda Research Laboratories, Takara Shuzo Co. and Toyobo Co.

pCEP97 DNA (0.5–1 μg) and each of said restriction enzymes were incubated in 20 μl of H buffer, M buffer, L buffer or S buffer at 37° C. for 60–180 minutes.

The digested samples were applied to 0.8% agarose gels and electrophoresed for 2 to 3 hours at 80 V in TPE buffer by a vertical gel electrophoresis system (0.3×16×16 cm). Detection of DNA bands in agarose gel was performed as described in Molecular Cloning, page 161 (1982).

The molecular sizes of restriction DNA fragments were determined by comparing their relative mobilities in agarose gels with those of λ-HindIII and cleaved pBR325 DNA fragments [Fragment sizes were determined from the DNA sequence of pBR325 [P. Prentki et al. Gene 14 (1981) 289]].

On the other hand, pCEP97 DNA, prepared in the above (1), was digested further with SalI and HindIII, and the small DNA fragment was electroeluted according to the method described in Molecular Cloning, page 164 (1982). Cleavage of that DNA fragment (2-3 μg) with restriction enzymes (AvaI, SmaI, ClaI, SacI and SacII) was performed as described above. Polyacrylamide gel electrophoresis (5% concentration) was performed as described in Molecular Cloning, page 173 (1982). The detection of DNA bands in poly-acrylamide gel was performed as described in Molecular cloning, page 161 (1982). The molecular sizes of DNA fragments were estimated by comparing their relative mobilities in polyacrylamide slab gel with those of pBR322-HaeIII [Sutcliffe, J. G. et al. Cold Spring Harbor Symp. Quant. Biol. 43 (1979) 77].

The results of agarose and polyacrylamide gel electrophoretic analysis of pCEP97 DNA cleaved with 20 restriction enzymes are summarized in Table 5. The number of restriction enzyme target sites of the ARS DNA fragment was determined by comparison with restriction digests of pCEP97 and pBR325 DNAs. The cleavage map for restriction enzymes and the fragment sizes for pCEP97 are shown in FIG. 5. Fragment sizes are expressed in Kbp.

(II) Construction of pCYG97.

(1) Cloning of $Km^R$-PvuII DNA fragment of Tn903 to pCEP97 DNA ($Ap^R Km^S$) (FIG. 2).

$Km^R$ gene (PvuII 1696 bp fragment) of Tn903 was purified from PvuII digested pAO43 DNA [A. Oka et al. J. Mol. Biol. 147 (1981) 217]. pCEP97 DNA, prepared in the above (I)-(1), (5 μg) was partially digested with PvuII (10 units) in 20 μl of H buffer at 37° C. for 60 minutes. $Km^R$-PvuII DNA fragment (1 μg) and the resulting PvuII partial digested pCEP97 DNA (5 μg) were ligated at 4° C. for 2 days in 40 μl of L buffer containing 0.5 mM ATP and 10 mM DTT, and T4 DNA ligase (BRL) (4 units). Then the ligated DNA was transformed to E. coli C600r−m− (ATCC 33525) according to the method described in Molecular Cloning, page 250. The transformed cells were plated on LB agar containing 20 μg/ml of ampicillin and incubated at 37° C. overnight. The ampicillin resistant colonies were transferred to LB agar containing 50 μg/ml of Kanamycin and LB agar containing 40 μg/ml of chloramphenicol. $Ap^R Km^R Cm^R$(one) and $Ap^R Km^R Cm^S$(239) colonies were obtained and the $Ap^R Km^R Cm^R$ clone was named pCYG97. pCYG97 DNA was isolated according to the method described in Advanced Bacterial Genetics, page 116.

(2) Determination of restriction enzyme map for pCYG97 DNA.

According to the same methods as those of the above (I)-(2) of Example 2, cleavage of pCYG97 DNA (0.5-1 μg), prepared as described above, with various restriction enzymes as specified in Table 5 (3-6 units) and agarose gel electrophoresis at 0.8% agarose and estimation of molecular sizes of DNA fragments were performed.

On the other hand, pCYG97 DNA, prepared in the above (1), was digested with SalI and EcoRI, and the small DNA fragment was purified according to the same method as described in (I)-(2) of Example 2. Cleavage of the resulting DNA fragment (2-3 μg) with restriction enzymes (HindIII, AvaI, SmaI, ClaI, SacI and SacII) was performed as described above. Polyacrylamide gel electrophoresis (5% concentration) and estimation of molecular sizes of DNA fragments were performed according to the method described in Sutclaffe, J. G. et al. Cold Spring Harbor Symp. Quant. Biol. 43 (1979) 77.

Results of agarose and polyacrylamide gel electrophoretic analysis of pCYG97 DNA cleaved with 20 restriction enzymes are summarized in Table 5. Number of restriction enzyme target sites of ARS DNA fragment was determined by comparison with those of pCYG97, pCEP97 and $Km^R$-PvuII DNA fragment (Fragment sizes were determined from DNA sequence for Tn903 {A. Oka et al. J. Mol. Biol. 147 (1981) 217}). The cleavage map for restriction enzymes and those fragment sizes for pCYG97 DNA are shown in FIG. 6. Fragment sizes are expressed in Kbp.

TABLE 5

Restriction Enzyme Target Sites of pCYG97 and pCEP97 DNAs.

| Restriction Enzyme | Sequence[1] | Number of Restriction Enzyme Target Sites | |
|---|---|---|---|
| | | pCYG97 | pCEP97 |
| AatII | GACGT↓C | 1 (0)[2] | 1 (0)[2] |
| AccI | GT↓QRAC | 2 (0) | 2 (0) |
| AvaI | C↓YCGUG | 4 (1) | 2 (1) |
| BalI[3] | TGG↓CCA | 2 (0) | 2 (0) |
| BamHI | G↓GATCC | 0 (0) | 0 (0) |
| BclI[3] | T↓GATCA | 2 (1) | 2 (1) |
| BglII | A↓GATCT | 0 (0) | 0 (0) |
| ClaI | AT↓CGAT | 3 (1) | 2 (1) |
| EcoRI | G↓AATTC | 1 (0) | 1 (0) |
| EcoRV[3] | GAT↓ATC | 1 (0) | 1 (0) |
| HincII | GTYUAC | 2 (0) | 2 (0) |
| HindIII | A↓AGCTT | 2 (0) | 1 (0) |
| HpaI | GTT↓AAC | 0 (0) | 0 (0) |
| KpnI | GGTAC↓C | 0 (0) | 0 (0) |
| MluI | A↓CGCGT | 2 (0) | 0 (0) |
| PstI | CTGCA↓G | 1 (0) | 1 (0) |
| PvuII | CAG↓CTG | 3 (0) | 2 (0) |
| SacI | GAGCT↓C | 1 (1) | 1 (1) |
| SacII | CCGC↓GG | 2 (2) | 2 (2) |
| SalI | G↓TCGAC | 1 (0) | 1 (0) |
| ScaI[3] | AGT↓ACT | 2 (0) | 2 (0) |
| SmaI | CCC↓GGG | 2 (1) | 1 (1) |
| SphI | GCATG↓C | 1 (0) | 1 (0) |
| StuI[3] | AGG↓CCT | 2 (0) | 0 (0) |
| XbaI[3] | T↓CTAGA | 0 (0) | 0 (0) |
| XhoI | C↓TCGAG | 1 (0) | 0 (0) |
| XmaIII[3] | C↓GGCCG | 3 (1) | 3 (1) |

[1]Q: A or C, R: G or T, Y: Py, U: Pu.
[2]( ): Number of restriction enzyme target sites of ARS DNA fragment.
[3]Restriction enzyme target sites were determined from DNA sequence.

TABLE 6

Dose Response in pCYG97 DNA Transformation to S. cerevisiae YNN27

| DNA | DNA Amount (mcg) | $G418^R$ Transformants (CFU[1]) |
|---|---|---|
| pCYG97 | 0.50 | $1.1 \times 10^4$ |
| | 0.050 | $3.0 \times 10^3$ |
| | 0.005 | $2.2 \times 10^2$ |
| pBR322 | 5.0 | 1 |

[1]CFU; colony forming units.

(III) Transformation of pCYG97 DNA to *S. cerevisiae* YNN 27. (α, trp 1-289, ura 3-52, gal 2) [D. T. Stinchcomb et al. Proc. Natl. Acad. Sci. USA 77 (1980) 4559].

(1) Yeast transformation

Sterile YEPD medium (20 ml) containing 10 μg/ml of uracil and 40 μg/ml of tryptophan was inoculated from an agar slant of *S. cerevisiae* YNN27 and cultured for 6 hours at 30° C. Then $1 \times 10^6$ cells were transferred to 100 ml of sterile YEPD medium supplemented uracil and tryptophan, and cultured overnight at 30° C. in 500 ml shaking flask. Cells were harvested by low speed centrifugation, suspended in 100 ml of new medium indicating above and cultured for 3 hours at 30° C.

Cells were harvested by centrifugation, washed twice with 50 ml of YP buffer, suspended in 50 ml of YP buffer containing 55 mM 2-mercaptoethanol and gently shaken at 30° C. for 30 minutes. Then the cells were harvested, suspended in 19 ml of YP buffer containing 75 mM 2-mercaptoethanol and 210 μg/ml of Zymolyase 5,000 (Seikagaku Kogyo Co.), and gently shaken at 30° C. for 10 minutes. The protoplasts were harvested by low speed centrifugation, washed twice with YP buffer and suspended in 0.6 ml of 2M sorbitol buffer.

DNA solution (10 μl) (each amount as specified in Table 6 of pCYG97 DNA, prepared in the above (II)-(1), and 5 μg of carrier pBR322 DNA) and 2M sorbitol buffer (20 μl) were mixed. The mixed DNA solution (30 μl) and the protoplast suspension (60 μl) were mixed, and incubated at room temperature for 10 minutes. Then one ml of 20% PEG 4,000 solution containing 10 mM Tris-HCl (pH 7.5) and 10 mM $CaCl_2$ was added to the reaction mixture, and incubated at room temperature for 20 minutes. The resulting transformed protoplasts were harvested by low speed centrifugation and suspended in 0.4 ml of 2M sorbitol buffer.

(2) Selection of the antibiotic G418-resistant transformants.

Selection of $G418^R$ transformants were performed according to the method of Webster and Dickson (Gene 26 (1983) 243). Transformed cells, prepared in the above (III)-(1), (0.2 ml) were diluted into 8 ml of regeneration agar and poured on top of a YEPD base plate (15 ml) supplemented 10 μg/ml uracil and 40 μg/ml of tryptophan. After solidification, an additional 8 ml of YEPD agar was poured onto the plate and incubated overnight at 30° C. Antibiotic G418 (GIBCO Lab.) was then administered by spreading 10 mg from a stock 100 mg/ml solution on top of each plate. Transformants appeared within 3-4 days at 30° C.

The effect of pCYG97 DNA amounts on the frequency of transformation to *S. cerevisiae* YNN27 is shown in Table 6 compared with pBR322 DNA. pCYG97 DNA was efficiently transformed to G418 resistance for *S. cerevisiae* YNN27.

(IV) Determination of DNA Sequence of ARS of pCYG97.

DNA sequence of ARS of pCYG97 was determined according to Maxam-Gilbert method [A. M. Maxam and W. Gilbert, Methods in Enzymology, 65, 499 (1980], and dideoxy sequencing method using M13mp10 and M13mp11 vectors [J. Messing, Methods in Enzymology, 101, 78 (1983)].

The DNA sequence of ARS of pCYG97 is shown in FIG. 8.

(V) Transformation of pCYG97 DNA to *Acremonium chrysogenum* ATCC11550

1. Buffer and Medium.

| CORN STEEP MEDIUM | CSL | 30 g/l |
| --- | --- | --- |
| | Glucose | 10 g/l |
| | Starch | 30 g/l |
| | pH 6.8 | |
| | $CaCO_3$ | 5 g/l |
| YPS MEDIUM | Sucrose | 20 g/l |
| | Polypeptone | 10 g/l |
| | Yeast Extract | 5 g/l |
| | $K_2HPO_4$ | 1 g/l |
| | $MgSO_4 7H_2O$ | 1 g/l |
| | pH 7.0 | |
| PROTOPLAST BUFFER | KCl | 0.6 M |
| | $MgCl_2$ | 10 mM |
| | $CaCl_2$ | 25 mM |
| BRM (Regeneration Medium) | | |
| A: | $NaNO_3$ | 2 g/900 ml |
| | $KH_2PO_4$ | 1 g/900 ml |
| | Sucrose | 275 g/900 ml |
| | Casamino Acids | 10 g/900 ml |
| | Agar | 7.5 g/900 ml |
| | pH 6.0 | |
| B: | Glucose | 200 g/l |
| | $MgCl_2$ | 20 mM |
| | $CaCl_2$ | 50 mM |

A, B: separately autoclaved
900 ml of A and 100 ml of B were mixed.

2. Methods and Results.

(1) Protoplast Formation.

A sterile corn steep medium (50 ml) was inoculated with mycelium from agar slant of *A. chrysogenum* ATCC11550 and cultured at 30° C. for 96 hours in 250 ml shaking flask. Five ml of this preculture in corn steep medium was transferred to 50 ml of sterile YPS medium and cultured at 25° C. for 24 hours as described above. Mycelium was harvested by centrifugation, washed with sterile water, suspended in 15 ml of 10 mM dithiothreitol solution and gently shaken at 30° C. for 1 hour. Then the mycelium was centrifuged, washed and resuspended in 20 ml of protoplast buffer containing 20 mg of Zymolyase 20T (Seikagaku Kogyo). After gently shaken at 30° C. for 2 hours, the protoplasts were harvested by low speed centrifugation, washed with protoplast buffer and resuspended in 0.5 ml of protoplast buffer.

(2) Transformation.

The protoplast suspension (100 μl) and plasmid DNA pCYG97 (10 μl, about 5 μg DNA) were mixed and incubated at room temperature for 10 minutes. Then 1 ml of 20% polyethyleneglycol (PEG) 4000 solution containing 25 mM $CaCl_2$ (pH 6.3) was added to the mixture. After 20 minutes at room temperature, the resulting transformed protoplasts were centrifuged and resuspended in 0.9 ml of protoplast buffer.

(3) Selection of the antibiotic G418 resistant transformants.

The transformed cells (0.2 ml) were poured on regeneration agar (15 ml of BRM) plates. Then 5 ml of BRM was poured. After incubation at 30° C. overnight, aliquots (0.2 ml of antibiotic G418, GIBCO Lab.) were spreaded on each plate. Plates were incubated at 30° C. for a week. The transformation frequency of pCYG97 DNA to *A. chrysogenum* ATCC11550 is shown in Table 7.

TABLE 7
Transformation Frequency of pCYG97 DNA to *Acremonium chrysogenum* ATCC11550[1].

| G418 Concentration (μg/ml) | DNA Amount | |
|---|---|---|
| | 1 μg pCYG97 DNA | 0 μg DNA |
| 300 | 3 | 0 |
| 100 | 130 | 17 |

[1]100 μl protoplast solutions of about 10^10 per ml were transformed. About 10^9 protoplasts per plate were plated.

Example 3

Plasmids pLEU135, pLEU97, pCEP97 and pCYG97 were each transformed into *E. coli* C600r⁻m⁻ (ATCC33525) by a conventional method to obtain the following microorganisms:

*Escherichia coli* C600r⁻m⁻ (pLEU135)
*Escherichia coli* C600r⁻m⁻ (pLEU97)
*Escherichia coli* C600r⁻m⁻ (pCEP97)
*Escherichia coli* C600r⁻m⁻ (pCYG97)

We claim:

1. A DNA fragment which functions as an autonomous replication sequence (ARS) in *Saccharomyces cerevisiae* and *Acremonium chrysogenum*, characterized as follows:
   (a) said ARS is prepared by digesting partially a chromosomal DNA of the *Acremonium chrysogenum* ATCC 11550 with restriction enzyme Sau 3A,
   (b) the molecular size of said ARS is about 1.39 Kbp, and
   (c) the DNA sequence of said ARS is as follows:

| 10 | 20 | 30 |
|---|---|---|
| GATCTCGGCG | AGCGGGTGAC | GGACGGGTTG |
| CTAGAGCCGC | TCGCCCACTG | CCTGCCCAAC |
| 40 | 50 | 60 |
| CTAGCGTTTA | CCAAGCCGGG | TCACACGCCG |
| GATCGCAAAT | GGTTCGGCCC | AGTGTGCGGC |
| 70 | 80 | 90 |
| CGGCTTGGCA | GGEAGCAGCC | ACTGTTACTA |
| GCCGAACCGT | CCETCGTCGG | TGACAATGAT |
| 100 | 110 | 120 |
| CTTGCATGTG | GGCTGATTGA | AAATCCCGGA |
| GAACGTACAC | CCGACTAACT | TTTAGGGCCT |
| 130 | 140 | 150 |
| ACCGATGGAT | GCTTCCCCCG | GGGATGCCGC |
| TGGCTACCTA | CGAAGGGGGC | CCCTACGGCG |
| 160 | 170 | 180 |
| TTCTTTCTCT | CTCTCGGCCG | CGGGAAGGTA |
| AAGAAAGAGA | GAGAGCCGGC | GCCCTTCCAT |
| 190 | 200 | 210 |
| TGCGTTGCCC | CCGGCCATAA | TAGTCGTCAA |
| ACGCAACGGG | GGCCGGTATT | ATCAGCAGTT |
| 220 | 230 | 240 |
| GCGGAAGGCC | AGCATTTGAT | CAGTAAAAAT |
| CGCCTTCCGG | TCGTAAACTA | GTCATTTTTA |
| 250 | 260 | 270 |
| ATCGGAATGA | TAAGTAATAG | ATTTTAAATT |
| TAGCCTTACT | ATTCATTATC | TAAAATTTAA |
| 280 | 290 | 300 |
| TACTATATTA | TATTGTATTT | TTTTCCCTAT |
| ATGATATAAT | ATAACATAAA | AAAAGGGATA |
| 310 | 320 | 330 |
| TATTAGTTCT | AATAAATAGG | TCAATTTAGA |
| ATAATCAAGA | TTATTTATCC | AGTTAAATCT |
| 340 | 350 | 360 |
| TAATAATCTT | ACTTTATTAA | ATTTAAATTG |
| ATTATTAGAA | TGAAATAATT | TAAATTTAAC |
| 370 | 380 | 390 |
| ATTTAAAGAA | TATAACAAAC | TATATTTTCT |
| TAAATTTCTT | ATATTGTTTG | ATATAAAAGA |
| 400 | 410 | 420 |
| CAAATAATTA | AAATATTTCC | CTGATTCATT |
| GTTTATTAAT | TTTATAAAGG | GACTAAGTAA |
| 430 | 440 | 450 |
| TTTAATTAAT | TCATTCCACA | TTTTTTTCAA |
| AAATTAATTA | AGTAAGGTGT | AAAAAAAGTT |
| 460 | 470 | 480 |
| AATAAGATGA | TTTAATTTTA | AAAATGTATT |
| TTATTCTACT | AAATTAAAAT | TTTTACATAA |
| 490 | 500 | 510 |
| TAAGTATTTA | AAAGTATAAT | TAATGTATTT |
| ATTCATAAAT | TTTCATATTA | ATTACATAAA |
| 520 | 530 | 540 |
| TCTTTTTTTT | ATAAAATCTT | TTACAAAAAA |
| AGAAAAAAAA | TATTTTAGAA | AATGTTTTTT |
| 550 | 560 | 570 |
| ATACTCATCA | TACATTTTAT | ATTTTTTATA |
| TATGAGTAGT | ATGTAAAATA | TAAAAAATAT |
| 580 | 590 | 600 |
| TAAAAGAGAA | TAAATATTTT | TTATATAATT |
| ATTTTCTCTT | ATTTATAAAA | AATATATTAA |
| 610 | 620 | 630 |
| ATTGTACAAA | GAAGTATAAT | TCTTAAACAA |
| TAACATGTTT | CTTCATATTA | AGAATTTGTT |
| 640 | 650 | 660 |
| GTTATAAGTT | ATTCTCATAT | TTAATAGATG |
| CAATATTCAA | TAAGAGTATA | AATTATCTAC |
| 670 | 680 | 690 |
| ATATTTTCTT | TTTAATGCTT | TTTTTTCTTT |
| TATAAAAGAA | AAATTACGAA | AAAAAAGAAA |
| 700 | 710 | 720 |
| ATTTATAGTA | AATAGTGTTA | TTTTTGCTTT |
| TAAATATCAT | TTATCACAAT | AAAAACGAAA |
| 730 | 740 | 750 |
| ACTATTTGTA | TATTTTATAT | TAGCATCACT |
| TGATAAACAT | ATAAAATATA | ATCGTAGTGA |
| 760 | 770 | 780 |
| TACAAAAATT | CTTCTTAAAA | AATTACGTCT |
| ATGTTTTTAA | GAAGAATTTT | TTAATGCAGA |
| 790 | 800 | 810 |
| TTTTTTTAGA | TATATAAATT | TAGTTTTACC |
| AAAAAAATCT | ATATATTTAA | ATCAAAATGG |
| 820 | 830 | 840 |
| TAAAAATTGA | CGGTTTTTAA | AAAATAAATT |
| ATTTTTAACT | GCCAAAAATT | TTTTATTTAA |
| 850 | 860 | 870 |
| AAAATAACTT | TTAATTATTT | TATTTATATT |
| TTTTATTGAA | AATTAATAAA | ATAAATATAA |
| 880 | 890 | 900 |
| TACAGTATTA | GCTGGTATAT | TTTTCATATT |
| ATGTCATAAT | CGACCATATA | AAAAGTATAA |
| 910 | 920 | 930 |
| ATTTTTATTA | AAAGAATATA | TAACATTTTT |
| TAAAAATAAT | TTTCTTATAT | ATTGTAAAAA |
| 940 | 950 | 960 |
| TCATTCTTTT | GAAAAAGCAG | GTAAATATTT |
| AGTAAGAAAA | CTTTTTCGTC | CATTTATAAA |
| 970 | 980 | 990 |
| CATATTATTT | ATAACAGTTA | ATTTAGGTTT |
| GTATAATAAA | TATTGTCAAT | TAAATCCAAA |
| 1000 | 1010 | 1020 |
| TAAACCAGAA | GTTCTGATAT | TTTTATTTAA |
| ATTTGGTCTT | CAAGACTATA | AAAATAAATT |
| 1030 | 1040 | 1050 |
| ATTATTCTTA | AAAATTTTCA | TTTTTATTTA |
| TAATAAGAAT | TTTTAAAAGT | AAAAATAAAT |
| 1060 | 1070 | 1080 |
| TTATTTATTT | CTTTTTATTT | CTTTTTATAT |
| AATAAATAAA | GAAAAATAAA | GAAAAATATA |
| 1090 | 1100 | 1110 |
| GCTTATTATA | GCTTTAACCT | ATAGCCATAA |
| CGAATAATAT | CGAAATTGGA | TATCGGTATT |
| 1120 | 1130 | 1140 |
| AAATGTTGGG | TAGTTTAAAA | GGATTATCAT |
| TTTACAACCC | ATCAAATTTT | CCTAATAGTA |
| 1150 | 1160 | 1170 |
| GTATTGCATA | ACATTCACCT | TATAGTCGTT |
| CATAACGTAT | TATAAGTGGA | ATATCAGCAA |
| 1180 | 1190 | 1200 |
| GAACGTTTTT | ATTTTATAAC | ATATGCTAAA |
| CTTGCAAAAA | TAAAATATTG | TATACGATTT |
| 1210 | 1220 | 1230 |
| ATAAATTCCG | CTTCAAATTT | ACTATCTTAA |
| TATTTAAGGC | GAAGTTTAAA | TGATAGAATT |
| 1240 | 1250 | 1260 |

| -continued | | |
|---|---|---|
| GTAATTTTJG | AAATTTACCC | AATTTATATC |
| CATTAAAAKC | TTTAAATGGG | TTAAATATAG |
| 1270 | 1280 | 1290 |
| AATTATTTTA | AGAGCTCTTA | GCTCAAATAA |
| TTAATAAAAT | TCTCGAGAAT | CGAGTTTATT |
| 1300 | 1310 | 1320 |
| AATATTAAAG | GACAAACATC | CCTAGCGTAG |
| TTATAATTTC | CTGTTTGTAG | GGATCGCATC |
| 1330 | 1340 | 1350 |
| CTTTTCCAAT | AATCCAAGAT | CCGTTAAATT |
| GAAAAGGTTA | TTAGGTTCTA | GGCAATTTAA |
| 1360 | 1370 | 1380 |

| -continued | | |
|---|---|---|
| ATCGATGCTA | TTTATACCTT | AACAAGTGCT |
| TAGCTACGAT | AAATATGGAA | TTGTTCACGA |
| 1390 | 1400 | |
| CTGTTACGAG | ATC | |
| GACAATGCTC | TAG. | |

2. Hybrid plasmid pLEU97.
3. Hybrid plasmid pCEP97.
4. Hybrid plasmid pCYG97.
5. *Escherichia coli* C600r−m− (pLEU97).
6. *Escherichia coli* C600r−m− (pCEP97).
7. *Escherichia coli* C600r−m− (pCYG97).

* * * * *